US011579108B2

(12) United States Patent
Smith et al.

(10) Patent No.: US 11,579,108 B2
(45) Date of Patent: Feb. 14, 2023

(54) APPARATUS FOR MONITORING A FLUID

(71) Applicant: 4T2 SENSORS LTD, Sutton Coldfield (GB)

(72) Inventors: Alexander Edward Smith, Sutton Coldfield (GB); Maxim Harry Joseph Swinbourne, Sutton Coldfield (GB)

(73) Assignee: 4T2 SENSORS LTD, Sutton Coldfield (GB)

( * ) Notice: Subject to any disclaimer, the term of this patent is extended or adjusted under 35 U.S.C. 154(b) by 235 days.

(21) Appl. No.: 16/763,118

(22) PCT Filed: Nov. 15, 2018

(86) PCT No.: PCT/GB2018/053316
§ 371 (c)(1),
(2) Date: May 11, 2020

(87) PCT Pub. No.: WO2019/097239
PCT Pub. Date: May 23, 2019

(65) Prior Publication Data
US 2020/0393398 A1  Dec. 17, 2020

(30) Foreign Application Priority Data

Nov. 15, 2017 (GB) ...................... 1718916

(51) Int. Cl.
*G01N 27/22* (2006.01)
*G01N 27/04* (2006.01)
(Continued)

(52) U.S. Cl.
CPC ......... *G01N 27/221* (2013.01); *G01N 27/045* (2013.01); *G01N 27/06* (2013.01); *G01N 27/228* (2013.01); *G01N 33/2847* (2013.01)

(58) Field of Classification Search
CPC .. G01N 27/221; G01N 27/228; G01N 27/045; G01N 27/06; G01N 33/2847
See application file for complete search history.

(56) References Cited

U.S. PATENT DOCUMENTS 3,691,841 A   9/1972 Lorenzino et al.
4,496,454 A   1/1985 Berger
(Continued)

FOREIGN PATENT DOCUMENTS

CN    205080193 U    3/2016
CN    106154048 A   11/2016
(Continued)

OTHER PUBLICATIONS

Patents Act 1977: Combined Search and Examination Report under Sections 17 and 18(3), UKIPO Application No. GB1718916.8, dated May 8, 2018, 5 pp.
(Continued)

*Primary Examiner* — Feba Pothen
(74) *Attorney, Agent, or Firm* — Myers Bigel, P.A.

(57) ABSTRACT

Apparatus for measuring at least one property of a fluid comprises a capacitive fluid sensor (110) comprising a first electrode (111) and a second electrode (112) with a sensing region (113) between the electrodes. The apparatus comprises an alternating signal source (120) configured to apply an alternating drive signal to the capacitive fluid sensor (110). The apparatus comprises a processing apparatus (200) configured to receive a sense signal from the capacitive fluid sensor (110) and the alternating drive signal. The processing apparatus (200) is configured to: determine a complex difference signal comprising an in-phase difference component between the drive signal and the sense signal and a quadrature difference component between the drive signal and the sense signal; determine the at least one property of the fluid based on both the in-phase phase difference com-
(Continued)

ponent and the quadrature difference component of the difference signal.

20 Claims, 12 Drawing Sheets

(51) Int. Cl.
*G01N 27/06* (2006.01)
*G01N 33/28* (2006.01)

(56) References Cited

U.S. PATENT DOCUMENTS

| | | | |
|---|---|---|---|
| 5,565,768 A * | 10/1996 | Kadar | G01N 15/1031 |
| | | | 323/369 |
| 5,609,576 A | 3/1997 | Voss et al. | |
| 5,677,631 A | 10/1997 | Reittinger et al. | |
| 6,691,040 B2 | 2/2004 | Bosetto et al. | |
| 7,043,402 B2 * | 5/2006 | Phillips | G01N 27/02 |
| | | | 702/65 |
| 2002/0125899 A1 | 9/2002 | Lvovich et al. | |
| 2004/0012399 A1 | 1/2004 | Lin et al. | |
| 2005/0264302 A1 | 12/2005 | Mohajer et al. | |
| 2008/0116908 A1 | 5/2008 | Potyrailo et al. | |
| 2008/0197863 A1 | 8/2008 | Lin et al. | |
| 2009/0048786 A1 | 2/2009 | Nardo et al. | |
| 2009/0107666 A1 | 4/2009 | Tchakarov et al. | |
| 2010/0188111 A1 | 7/2010 | Fougere | |
| 2010/0295565 A1 | 11/2010 | Drack | |
| 2010/0321036 A1 | 12/2010 | Camp | |
| 2012/0064567 A1 * | 3/2012 | Stakenborg | G01N 15/1245 |
| | | | 435/306.1 |
| 2012/0114089 A1 | 5/2012 | Potyrailo et al. | |
| 2012/0197566 A1 | 8/2012 | Habic | |
| 2014/0196522 A1 | 7/2014 | Borini et al. | |
| 2015/0002178 A1 | 1/2015 | Herb et al. | |
| 2015/0346129 A1 | 12/2015 | Kersey | |
| 2016/0115395 A1 | 4/2016 | Rustad et al. | |
| 2018/0052133 A1 | 2/2018 | Godfrey et al. | |
| 2019/0041880 A1 | 2/2019 | Grassi | |

FOREIGN PATENT DOCUMENTS

| | | |
|---|---|---|
| CN | 108152361 A | 6/2018 |
| DE | 27 01 197 A1 | 7/1978 |
| JP | 8-210890 A | 8/1996 |
| KR | 10-2018-0038839 A | 4/2018 |
| WO | 03/001167 A2 | 1/2003 |
| WO | 2008/101161 A1 | 8/2008 |
| WO | 2012/007347 A1 | 1/2012 |
| WO | 2020/084281 A2 | 4/2020 |

OTHER PUBLICATIONS

International Search Report and Written Opinion of the International Searching Authority, International Application No. PCT/GB2018/053316, dated Feb. 4, 2019, 14 pp.

Patents Act 1977: Combined Search and Examination Report under Sections 17 and 18(3), UKIPO Application No. GB1819732.7, dated Jun. 4, 2019, 11 pp.

Mleettechniekinfo, "Measuring capacitance & ESR", Jan. 20, 2014, 6 pp., available online from https://meettechniek.info/passive/capacitance.html [accessed May 31, 2019].

Fuchs et al., "Capacitive Sensing In Process Instrumentation", Metrology and Measurements Systems, vol. XVI, No. 4, 2009, pp. 557-568.

Lyons, "A Quadrature Signals Tutorial: Complex, But Not Complicated", DSP Related.com, Apr. 12, 2013, 27 pp., available online from https://www.dsprelated.com/showarticle/192.php [accessed May 31, 2019].

Invitation to Pay Additional Fees and, where Applicable, Protest Fee, International Application No. PCT/GB2019/052979, Feb. 19, 2020, 11 pp.

Jaegle et al., "Thermal-electrical impedance spectroscopy for fluid characterisation", Procedia Engineering (Special Issue: Proceedings of the 30th anniversary Eurosensors Conference—Eurosensors 2016, 4-7. Sep. 2016, Budapest, Hungary), vol. 168, pp. 770-773.

* cited by examiner

APPARATUS FOR MONITORING A FLUID

RELATED APPLICATIONS

This application is a 35 U.S.C. § 371 national stage application of PCT Application No. PCT/GB2018/053316, filed on Nov. 15, 2018, which claims priority from Great Britain Patent Application No. 1718916.8, filed on Nov. 15, 2017, the contents of which are incorporated herein by reference in their entireties. The above-referenced PCT International Application was published in the English language as International Publication No. WO 2019/097239 A1 on May 23, 2019.

TECHNICAL FIELD

The present invention relates to apparatus and a method for monitoring a fluid.

BACKGROUND

There are various applications where it is desirable to monitor a property of a fluid. One example application is a machining operation which uses a cutting fluid. The cutting fluid is an emulsion of oil and water. It is required to maintain a ratio of oil to water in the cutting fluid within certain bounds. A sensing system measures the ratio of oil to water in the cutting fluid and an adjustment is made to the ratio based on the measurement.

One known way of measuring a property of a fluid is by optical technology. An optical source emits an optical signal into a fluid sample and an optical detector can determine a refractive index, or some other optical property, of the fluid sample. Another known way of measuring a property of a fluid is by radio frequency (RF) technology, such as a sensor which operates in the microwave frequency band.

Another way of measuring a property of a fluid is by an electrical sensing system, using a capacitive sensor. US 2010/018811 A1 describes apparatus for the measurement of electrical conductivity and dielectric constant of a lubricating oil or a fuel. The apparatus provides two distinct measurement circuits for conductivity measurement and dielectric constant measurement. US 2004/0012399 A1 describes an apparatus for measuring complex impedance of a fuel. In both of these, the fluid under test is a high impedance fluid.

An electrical sensing system typically only works with high impedance fluids, i.e. fluids with a relatively low conductivity. Therefore, in applications with high conductivity fluids, such as the cutting fluid application described above, it is typical to use optical or RF technology to monitor the fluid. This increases cost of the monitoring apparatus.

It is an aim of the present invention to address disadvantages associated with the prior art.

SUMMARY OF THE INVENTION

An aspect provides apparatus for measuring at least one property of a fluid, the apparatus comprising:
 a capacitive fluid sensor comprising a first electrode and a second electrode with a sensing region between the electrodes;
 an alternating signal source configured to apply an alternating drive signal to the capacitive fluid sensor; and
 a processing apparatus configured to:
  receive a sense signal from the capacitive fluid sensor;
  receive the alternating drive signal;
  determine a complex difference signal comprising an in-phase difference component between the drive signal and the sense signal and a quadrature difference component between the drive signal and the sense signal;
  determine the at least one property of the fluid based on both the in-phase phase difference component and the quadrature difference component of the difference signal by compensating for an effect on the complex difference signal due to at least one parasitic element of the apparatus.

The complex difference signal may comprise a ratio of the sense signal and the drive/reference signal. The sense signal may be represented as a complex number with an in-phase component and a quadrature component. The drive signal may be represented as a complex number with an in-phase component and a quadrature component. The complex difference signal obtained by a ratio of the sense signal and the drive signal may also be represented as a complex number with an in-phase difference component and a quadrature difference component. The complex difference signal may represent (i) a phase difference between the sense signal and the drive/reference signal and (ii) a magnitude equal to a ratio of the magnitudes of the sense signal and the drive/reference signal.

Optionally, the processing apparatus is configured to determine an in-phase component of the sense signal and a quadrature component of the sense signal.

Optionally, the processing apparatus is configured to determine the in-phase component of the sense signal and the quadrature component of the sense signal by an averaging filtering operation performed over a plurality of cycles of the alternating drive signal.

Optionally, the processing apparatus is configured to determine an in-phase component of the drive signal and a quadrature component of the drive signal.

Optionally, the processing apparatus is configured to determine an in-phase component of the drive signal and a quadrature component of the drive signal by an averaging filtering operation performed over a plurality of cycles of the alternating drive signal.

Optionally, the processing apparatus is configured to:
 determine the in-phase component of the sense signal and the quadrature component of the sense signal by an averaging filtering operation performed over a plurality of cycles of the alternating drive signal;
 determine an in-phase component of the drive signal and a quadrature component of the drive signal by an averaging filtering operation performed over a plurality of cycles of the alternating drive signal;
 determine the in-phase difference component based on the filtered in-phase component of the sense signal and the filtered in-phase component of the drive signal; and
 determine the quadrature difference component based on the filtered quadrature component of the sense signal and the filtered quadrature component of the drive signal.

Optionally, the processing apparatus is configured to use the in-phase difference component and the quadrature difference component in an algorithmic model of the apparatus to determine the dielectric constant of the fluid, wherein the algorithmic model includes the at least one parasitic element of the apparatus.

Optionally, the processing apparatus is configured to use the in-phase difference component and the quadrature difference component in an algorithmic model of the apparatus to determine conductivity of the fluid, wherein the algorithmic model includes the at least one parasitic element of the apparatus.

Optionally, the processing apparatus is configured to compare the in-phase difference component and the quadrature difference component to a plurality of stored compensated data values to determine the dielectric constant of the fluid, wherein the stored compensated data values compensate for an effect of at least one parasitic element of the apparatus.

Optionally, the processing apparatus is configured to compare the in-phase difference component and the quadrature difference component to a plurality of stored compensated data values to determine conductivity of the fluid, wherein the stored compensated data values compensate for an effect of at least one parasitic element of the apparatus.

Optionally, the processing apparatus is configured to measure at least one property of a fluid with a conductivity of up to 200 mS/m.

Optionally, the processing apparatus is configured to sample the sense signal at a sampling frequency, and a frequency of the alternating current drive signal is higher than the sampling frequency.

Optionally, the processing apparatus is configured to:
provide a digital oscillator with an in-phase oscillator output and a quadrature oscillator output;
provide a phase-locked loop which is configured to use the in-phase oscillator output and the quadrature oscillator output to achieve synchronisation between the drive signal and the digital oscillator.

Optionally, the phase-locked loop is a Costas loop.

Optionally, the processing apparatus is configured to use the in-phase oscillator output and the quadrature oscillator output to process the sense signal when a locked synchronisation state has been achieved.

Optionally, the apparatus comprises an analogue-to-digital converter and the processing apparatus is configured to:
sample the sense signal at a first time and sample the drive signal at a second time which is offset from the first time; and
apply a correction factor to the sampled signals to correct for the offset times at which the signals were sampled.

Optionally, the parasitic element is lead inductance. The lead inductance is inductance of one or more of: a lead connecting the drive signal generator to the capacitive fluid sensor; a lead connecting the capacitive fluid sensor to the processing apparatus.

Optionally, the processing stage is a digital signal processing stage.

Optionally, the apparatus comprises a temperature sensor, and the processing apparatus is configured to:
determine temperature of the fluid;
determine conductivity using the determined temperature.

Optionally, the capacitive fluid sensor is configured to monitor a flowing fluid, wherein the first electrode and the second electrode define a fluid flow channel between the electrodes.

Optionally, the first electrode is a tubular electrode and the second electrode is located within the first electrode.

The processing apparatus may be configured to receive the alternating drive signal directly from the alternating signal source, or from some other node which is external to the capacitive fluid sensor. This provides the processing apparatus with a signal which is indicative of the drive signal. The processing apparatus can use the drive signal for comparison with the sense signal to determine the effect of the fluid on the capacitive fluid sensor.

Another aspect provides a processing apparatus for measuring at least one property of a fluid, the processing apparatus configured to:
receive a sense signal from a capacitive fluid sensor;
receive an alternating drive signal which has been applied to the capacitive fluid sensor;
determine a complex difference signal comprising an in-phase difference component between the drive signal and the sense signal and a quadrature difference component between the drive signal and the sense signal;
determine the at least one property of the fluid based on both the in-phase phase difference component and the quadrature difference component of the difference signal by compensating for an effect on the complex difference signal due to at least one parasitic element of the apparatus.

Another aspect provides a method of measuring at least one property of a fluid, the method comprising:
receiving a sense signal from a capacitive fluid sensor;
receiving an alternating drive signal which has been applied to the capacitive fluid sensor;
determining a complex difference signal comprising an in-phase difference component between the drive signal and the sense signal and a quadrature difference component between the drive signal and the sense signal;
determining the at least one property of the fluid based on both the in-phase phase difference component and the quadrature difference component of the difference signal by compensating for an effect on the complex difference signal due to at least one parasitic element of the apparatus.

Another aspect provides a computer program product comprising a machine-readable medium carrying instructions which, when executed by a processor, cause the processor to perform the method defined above or described herein.

Another aspect provides apparatus for measuring at least one property of a fluid, the apparatus comprising a processing apparatus configured to:
receive a sense signal from a capacitive fluid sensor;
receive an alternating drive signal which has been applied to the capacitive fluid sensor;
determine a complex difference signal comprising an in-phase difference component between the drive signal and the sense signal and a quadrature difference component between the drive signal and the sense signal;
determine the at least one property of the fluid based on both the in-phase phase difference component and the quadrature difference component of the difference signal by compensating for an effect on the complex difference signal due to at least one parasitic element of the apparatus.

An advantage of at least one example is that it is possible to measure dielectric constant for fluids with a high conductivity. Conventionally, it has not been possible to measure dielectric constant of a high conductivity fluid using a capacitive sensor as the effect of the fluid on a capacitive sensor has been considered too small to measure accurately. Also, parasitic elements of the apparatus can contribute to the measured signal, and can mask a signal contributed by the capacitive sensor. This makes it difficult to measure a contribution by the capacitive sensor.

The dielectric loss of the fluid is a function of its conductivity. Therefore, it is also possible to make high resolution measurements of conductivity without the need for platinum electrodes.

A relatively low radio frequency alternating frequency signal (e.g. <10 MHz), together with digital signal processing, allows measurements to be made using low cost readily available components.

In an aspect of the invention there is provided a cutting machine for performing a cutting operation comprising apparatus according to an aspect of the invention configured to measure at least one property of a cutting fluid employed in the cutting operation.

The cutting fluid may comprise an emulsion of oil in water.

Optionally, the apparatus is configured to provide an output in dependence on a proportion of oil: water in the cutting fluid.

The cutting machine may be configured automatically to increase the proportion of water in the cutting fluid when the proportion of water is outside a required limit.

A chemical plant comprising apparatus according to an aspect of the present invention configured to measure at least one property of a fluid.

A fluid manufacturing or processing plant comprising apparatus according to an aspect of the present invention configured to measure at least one property of a fluid.

Optionally, the fluid is beer, whiskey or a bio-fuel.

A machine comprising apparatus according to an aspect of the present invention configured to measure at least one property of a lubricant of the machine.

Optionally, the lubricant is gearbox oil.

The functionality described here can be implemented in hardware, software executed by a processing apparatus, or by a combination of hardware and software. The processing apparatus can comprise a computer, a processor, a state machine, a logic array or any other suitable processing apparatus. The processing apparatus can be a general-purpose processor which executes software to cause the general-purpose processor to perform the required tasks, or the processing apparatus can be dedicated to perform the required functions. Another aspect of the invention provides machine-readable instructions (software) which, when executed by a processor, perform any of the described methods. The machine-readable instructions may be stored on an electronic memory device, hard disk, optical disk or other machine-readable storage medium. The machine-readable medium can be a non-transitory machine-readable medium. The term "non-transitory machine-readable medium" comprises all machine-readable media except for a transitory, propagating signal. The machine-readable instructions can be downloaded to the storage medium via a network connection.

Within the scope of this application it is envisaged that the various aspects, embodiments, examples and alternatives, and in particular the individual features thereof, set out in the preceding paragraphs, in the claims and/or in the following description and drawings, may be taken independently or in any combination. For example features described in connection with one embodiment are applicable to all embodiments, unless such features are incompatible.

For the avoidance of doubt, it is to be understood that features described with respect to one aspect of the invention may be included within any other aspect of the invention, alone or in appropriate combination with one or more other features.

BRIEF DESCRIPTION OF THE DRAWINGS

One or more embodiments of the invention will now be described, by way of example only, with reference to the accompanying figures in which.

DETAILED DESCRIPTION

Figure 1:
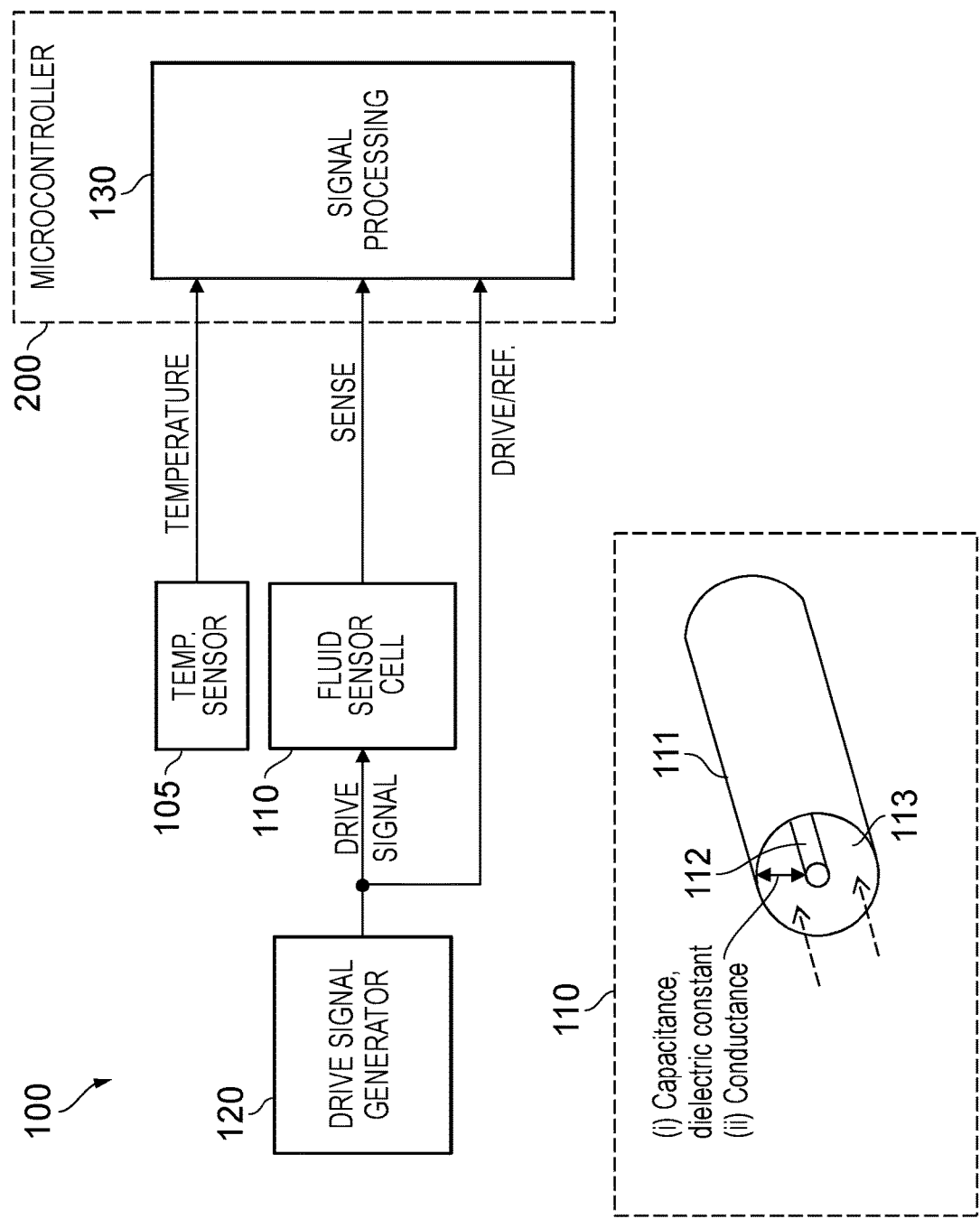
FIG. 1 shows a system for monitoring a fluid.

FIG. 1 shows a system 100 for monitoring a fluid, such as a liquid or a gas. The system 100 comprises a fluid sensor cell 110. FIG. 1 shows an example of a fluid sensor cell 110 which is configured for monitoring a flowing fluid. The fluid sensor cell 110 is a form of capacitive sensor. The sensor has a first, outer, electrode 111 and a second, inner, electrode 112. The outer electrode 111 is tubular. The inner electrode 112 is a cylindrical rod. The electrodes 111, 112 are coaxial. A fluid flow channel 113 is defined in the region between the electrodes 111, 112. Fluid can flow along the fluid flow channel 113. This allows measurements to be made without a need to interrupt a process which uses the fluid. For example, in the application of measuring a cutting fluid, the cutting fluid (or a portion of the cutting fluid) can be routed via the flow channel 113. The sensor cell 110 may have a different configuration. For example, a spaced-apart pair of linear electrodes (rods, plates or other shape). In a case of monitoring a static fluid, the sensor cell 110 does not have to include a flow channel.

The capacitive sensor 110 has two main properties: (i) capacitance; (ii) conductance. These properties will vary according to the type of fluid between the electrodes 111, 112. Capacitance of the sensor is the ability of the sensor to store electric charge. Capacitance varies according to the permittivity of the dielectric material between the electrodes 111, 112 of the capacitor. A dielectric material with a high dielectric constant (i.e. a good insulator) will increase the capacitance. Conductance is the flow of charge between the electrodes, through the dielectric material between the electrodes 111, 112. Conductance also depends on the properties of the dielectric material between the electrodes 111, 112 of the capacitor. A high impedance fluid will cause a small conductance between the electrodes 111, 112. A low impedance fluid will give a higher conductance between the electrodes 111, 112. For each of these properties, the dielectric material is the fluid between the electrodes 111, 112.

A drive signal generator 120 generates a drive signal. The drive signal is an alternating current electrical signal at a suitable frequency. The drive signal is applied to the fluid sensor cell 110. The drive signal may be applied to the inner electrode 112, with the outer electrode 111 connected to a reference ground. In an example of the present application the alternating current electrical signal has a frequency which is in the low radio frequency (RF) range, of less than 10 MHz, such as 5.05 MHz. The drive signal generator 120 can be implemented by a Direct Digital Synthesis integrated circuit feeding a wideband operational amplifier. Direct Digital Synthesis is a technique which generates a sinusoidal analogue signal using a sequence of digital values representing amplitude of the signal at points in time. The digital values are converted into an analogue signal by a digital-to-analogue converter. The digital values required to generate the signal may be stored, and retrieved from memory, or calculated on-the-fly using an algorithm.

A signal processing stage 130 is implemented, for example, by a microcontroller 200. The signal processing stage 130 receives an alternating electrical signal SENSE from the fluid sensor cell 110. The drive signal applied to the fluid sensor cell 110 will be modified by properties of the fluid in the fluid sensor cell 110. SENSE is indicative of the fluid. The signal processing stage 130 also receives the drive signal as a signal DRIVE or REF. It is possible to supply the drive signal by directly connecting an output of the drive signal generator 120 to the processing stage 130. Alternatively, the drive signal may be tapped from a different point, REF, in the system as described below.

Figure 2:
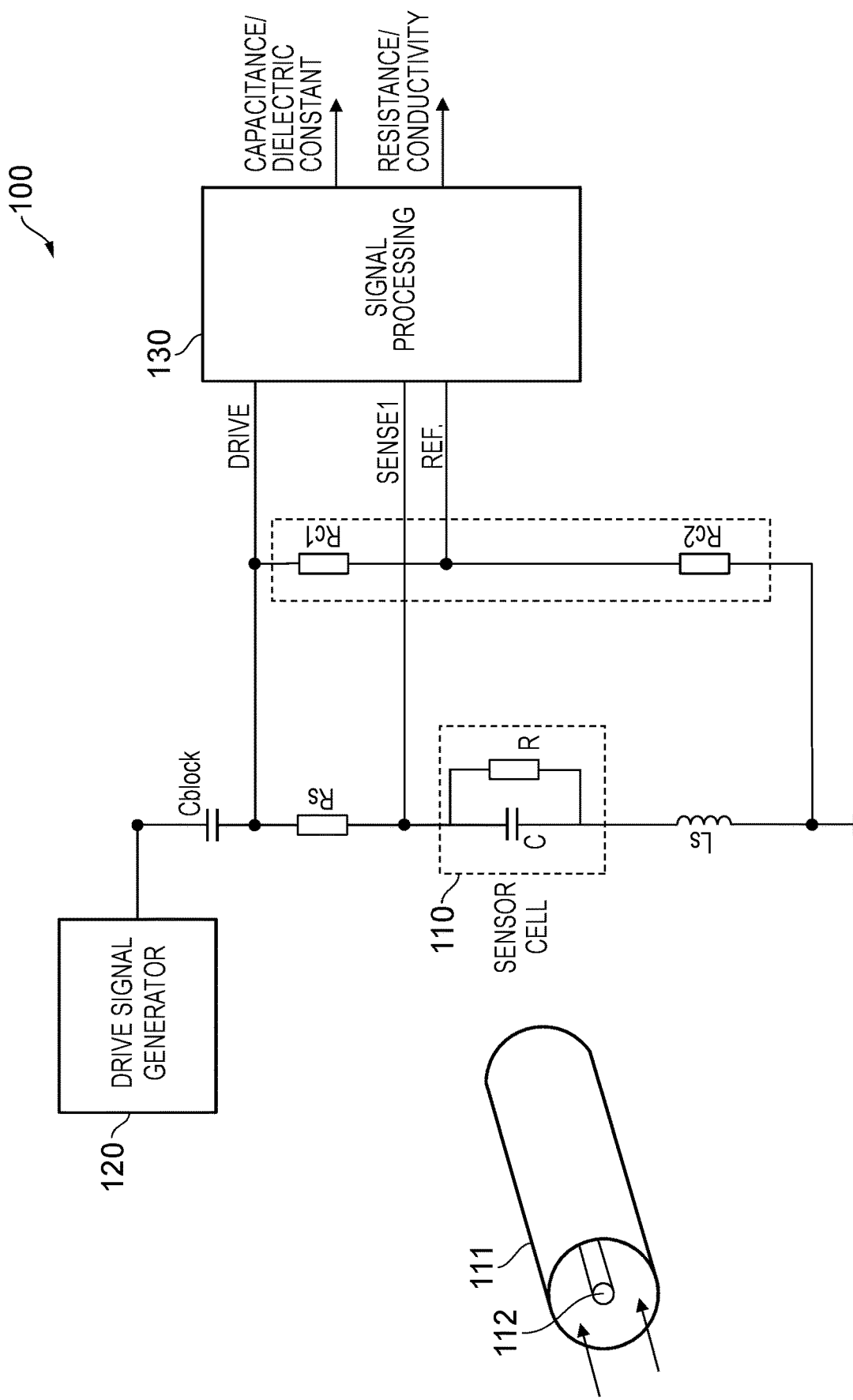
FIG. 2 shows a front-end of the system, showing analogue components.

FIG. 2 shows a schematic of the front-end of the system 100, showing analogue-domain components. The sensor cell 110 can be represented as an equivalent circuit network with a capacitance C in parallel with a resistance R. The value of C in this network is determined by the dielectric constant and R is a function of the conductivity of the fluid. $C_{block}$ is a DC blocking capacitor. $C_{block}$ is large (>10 nF) compared to the capacitance of the sensor cell 110 to ensure there is no DC bias on the fluid. A DC bias can cause unwanted electrolytic plating of the electrodes 111, 112.

The impedance of the sensor cell 110 equivalent circuit (R and C in parallel) can be expressed as:

$$Z = \left[\frac{1}{R} + j\omega C\right]^{-1}$$

where $\omega$ is $2\pi\times$ the drive signal frequency.

$R_s$ and Z form a potential divider and the voltage across Z is the main sensor feedback signal SENSE. Z is a complex impedance. $L_s$ is lead inductance from the connections to the sensor cell 110. $L_s$ also contributes (significantly) to phase and amplitude of SENSE. $L_s$ is a parasitic element of the apparatus.

Figure 3A:
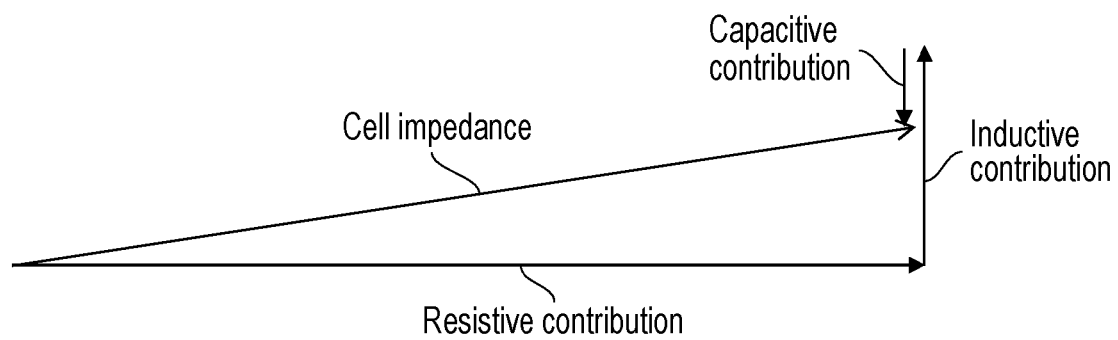
FIG. 3A shows impedance of the sensor cell and lead in the system of FIG. 1.
Figure 3B:
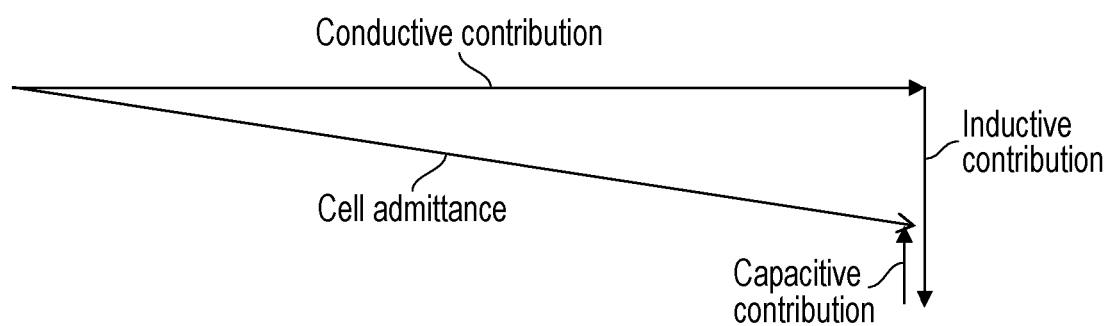
FIG. 3B shows admittance of the sensor cell and lead in the system of FIG. 1.

FIG. 3A shows a complex impedance of a combination of the sensor cell 110 and lead(s) when measuring fluids with high conductivities. This will be described in full detail below but, in summary, the complex impedance of the sensor cell 110 and lead has an in-phase/real component and a quadrature/imaginary component. The in-phase/real component is due to resistance of the sensor cell and lead. The quadrature/imaginary component is mainly due to capacitance of the sensor cell and inductance of the lead. FIG. 3B shows the corresponding complex admittance, where admittance is the reciprocal of the impedance, Y=1/Z. From FIG. 3A and FIG. 3B it can be seen that it is difficult to observe the contribution to the complex impedance made by the capacitive sensor cell C, which represents the fluid under test. The wanted capacitive contribution is masked by the unwanted parasitic inductive contribution. The main parasitic effects which need to be compensated for are lead inductance and input capacitance of the analogue-to-digital converter (ADC) used to measure the signals.

Figure 4:
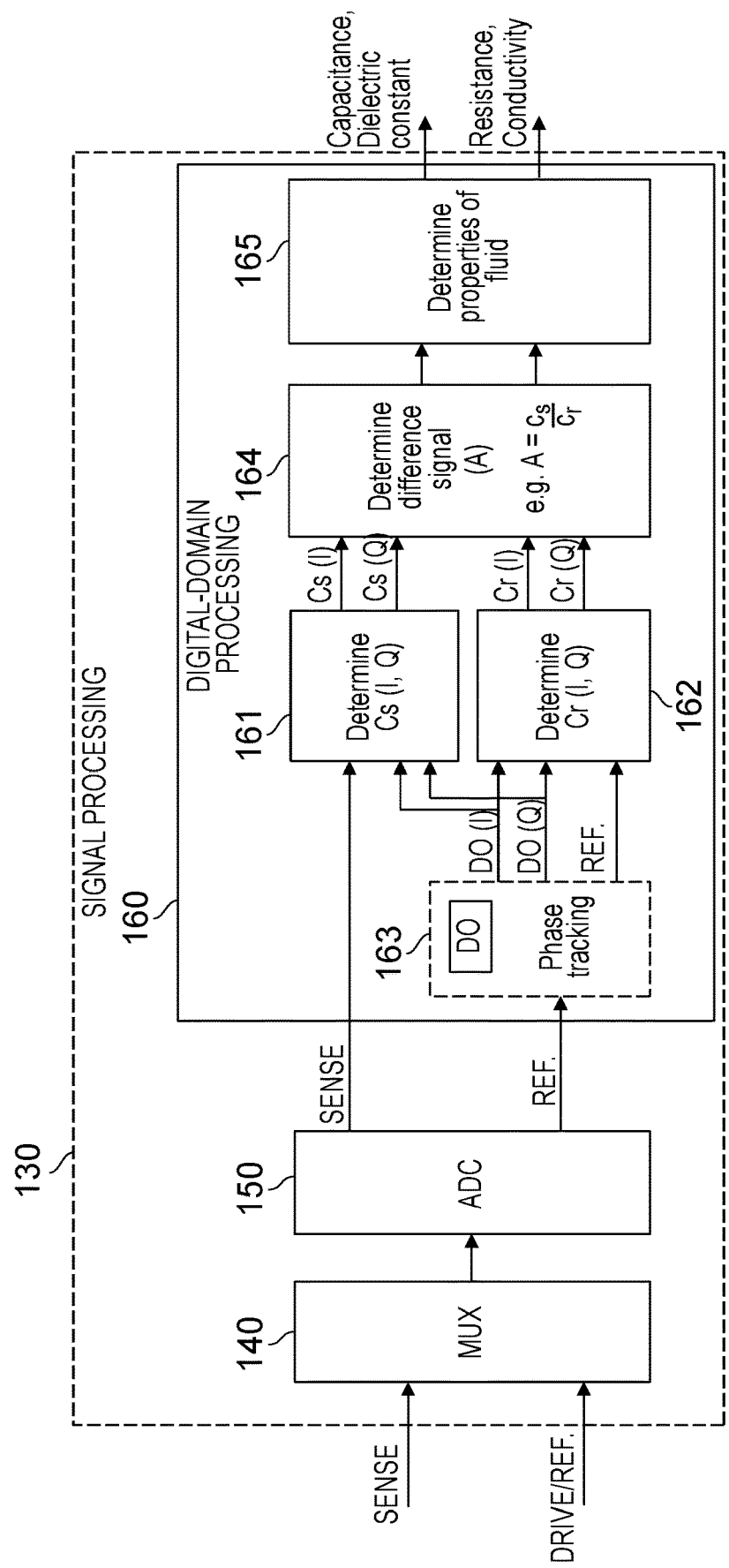
FIG. 4 shows signal processing in the system of FIG. 1.

FIG. 4 shows the signal processing stage 130. A multiplexer MUX 140 receives SENSE and DRIVE/REF as inputs and selectively outputs one of the input signals to an analogue-to-digital converter (ADC) 150. The ADC 150 outputs digital values. Outputs of the ADC 150 are applied to a digital-domain processing stage 160. A processing stage 161 determines in-phase (real) and quadrature (imaginary) components of the sense signal SENSE. These will be called Cs(I) and Cs(Q) respectively. A processing stage 162 determines in-phase (real) and quadrature (imaginary) components of the drive/reference signal. These will be called Cr(I) and Cr(Q) respectively. Processing stages 161, 162 perform Fourier analysis. Stage 163 includes a local digital oscillator, and acquires synchronisation between the local digital oscillator and the drive signal. Stage 163 outputs in-phase (I) and quadrature (Q) signals to stages 161 and 162. These outputs are labelled DO (I), DO (Q). A processing stage 164 determines in-phase (real) and quadrature (imaginary) components of a difference signal between the sense signal SENSE and the drive/reference signal. The difference signal represents a difference, in terms of amplitude and phase, between the drive signal applied to the sensor cell 110 and the signal across the sensor cell 110 due to the fluid. A processing stage 165 determines properties of the fluid. Stage 165 determines capacitance (dielectric constant) of the fluid using the I & Q values of the difference signal. Stage 165 can also determine resistance (conductivity) of the fluid using the I & Q values of the difference signal.

The output of stage 164 represents the measured impedance at the ADC 150, subject to a transformation caused by parasitic properties of the system. The output consists of two numbers corresponding to the real (in-phase, I) and imaginary (quadrature, Q) outputs of the Fourier analysis. There are several sources of parasitic properties of the system. Lead inductance $L_s$ (FIG. 2) is present as a property of wires connecting to the sensor. It has the effect of introducing an imaginary component which is a function of both frequency and conductivity. Its contribution to the imaginary components of the measurements is larger than the changes in capacitance (due to fluid) that are being measured. The ADC 150 has parasitic input capacitance that also causes a finite phase shift. The phase shift caused by the ADC will be a function of the output impedance of SENSE.

Figure 5:
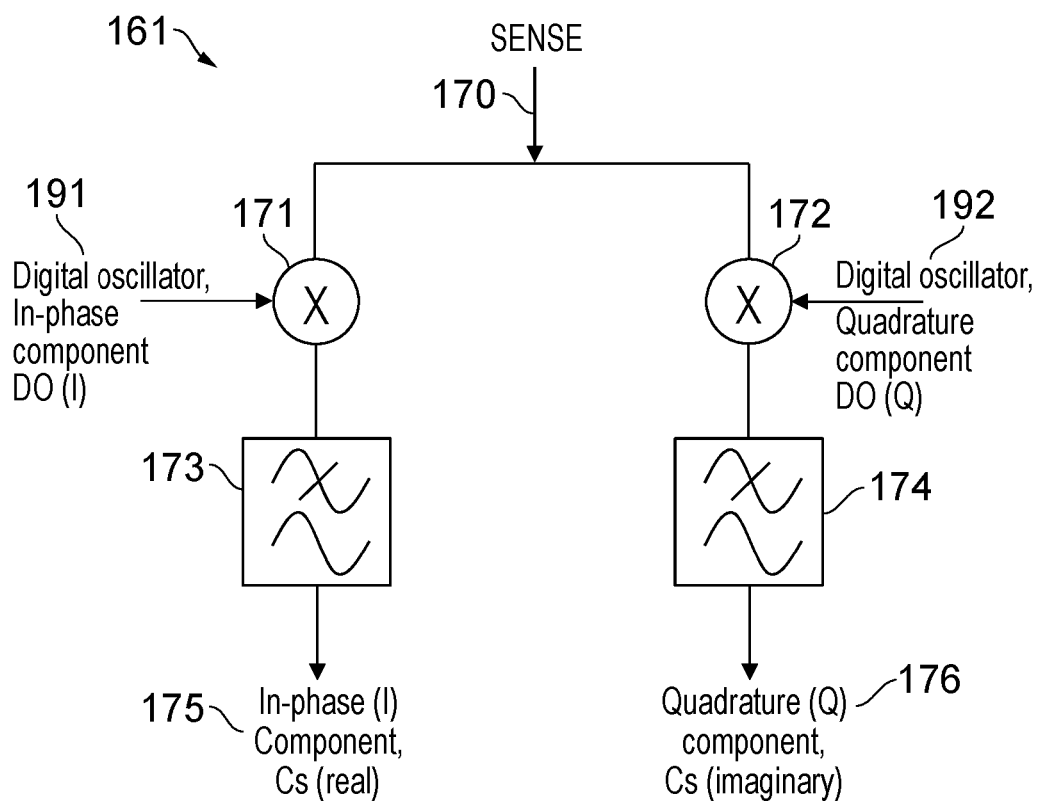
FIG. 5 shows a signal processing stage for the sensed signal.

FIG. 5 shows stage 161 of the digital-domain processing 160 in more detail. Samples of the digitised signal SENSE are received at an input 170. The processing proceeds in two arms: an in-phase arm and a quadrature arm. In the in-phase arm, SENSE is multiplied 171 with an in-phase (I) output of a digital oscillator, DO (I). An output of the multiplication is applied to a low-pass filter 173. An output 175 of the low-pass filter 173 provides an in-phase (I) component of the signal SENSE, called Cs(I). In the quadrature arm, SENSE is multiplied 172 with a quadrature (Q) component of a digital oscillator, DO (Q). An output of the multiplication is applied to a low-pass filter 174. An output 176 of the low-pass filter 174 provides a quadrature (Q) component of the signal SENSE, called Cs(Q). Each of the low-pass filters 173, 174 may be implemented as an Infinite Impulse Response (IIR) digital filter. Each of the low-pass filters 173, 174 has a time-averaging function on sample values applied to an input of the filter. As an example, the filter can perform a 'rolling' average on input values. Consider that the filter has an input x and an output x0. At each computation cycle:

$$x0=(\text{previous } x0)*0.999+0.001*x$$

In this simple example, the filter coefficient values are 0.999 and 0.001, with the two coefficients summing to 1. It will be understood that the digital filter can perform a different algorithm with different coefficient values and/or a higher number of computation stages. The low-pass filters 173, 174 can make it possible to determine a value of the I or Q component with a high degree of accuracy, by computing a value over a significant number of computations. For example, the output value of the filter may be computed over several thousand cycles of the drive signal SENSE. Stage 161 allows the circuit to tune in to the input signal within a very narrow frequency band and produces two output results representing the size of the in-phase (real) and quadrature (imaginary) components of the input signal. Reducing the bandwidth gives very accurate sub-quantisation level resolution.

Referring back to the example system of FIG. 1, the microcontroller 200 and the drive signal generator 120 can be implemented as separate integrated circuits. This means the drive signal generator 120 and the microcontroller 200 will each have a separate local oscillator (clock) which operates at a different rate and/or accuracy. This also means that the drive signal is asynchronous to the signal processing 130. The amplitude and phase of DRIVE is initially treated as unknown by the signal processing 130.

Figure 6:
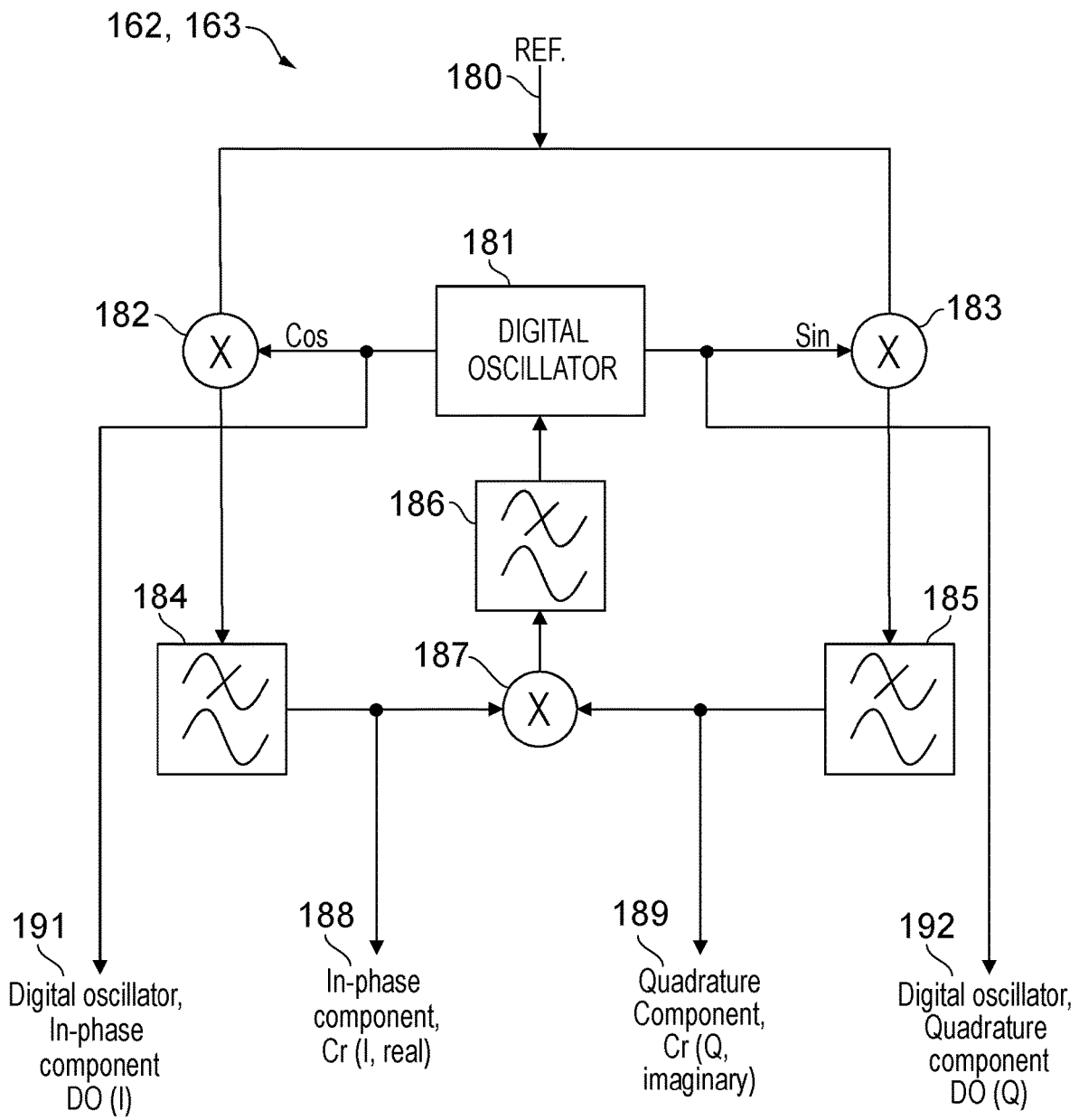
FIG. 6 shows a signal processing stage for the reference signal, and for synchronisation.

FIG. 4 and FIG. 6 show an additional stage 163 which can synchronise to REF. Referring to FIG. 6, the circuit 163 is a Costas loop. A Costas loop is a form of phase-locked loop which can digitally lock onto the drive signal (DRIVE or REF). An input 180 receives signal DRIVE representing the drive signal. A digital oscillator 181 outputs two data streams representing two sine waves: one in phase (Cos) and one in quadrature (Sin) to the drive signal. Each signal is multiplied 182, 183 with REF. Outputs of the multiplication are low-pass filtered 184, 185. Respective outputs of each low-pass filter 184, 185 are multiplied together 187 and applied to a low-pass filter 186. An output of low-pass filter 186 is applied as a control signal to the oscillator 181. The circuit of FIG. 6 performs two functions: (i) it achieves synchronisation between the digital oscillator and drive/reference signal REF; (ii) it determines in-phase component and a quadrature component of the drive/reference signal REF.

Multiplying both real and imaginary parts of the digital oscillator signal with the incoming drive signal REF and integrating over a number of samples yields the real and imaginary Fourier coefficients of the drive signal at that frequency. If the drive signal is in-phase and of equal frequency (i.e. a lock condition) then the real Fourier coefficient should be 0.5 and the imaginary coefficient should be 0. In practice, there is usually a difference between the signals, such as the drive signal leading or lagging the digital oscillator. It is possible to determine whether the drive/reference signal REF is leading or lagging the digital oscillator by looking at the value of the imaginary part. An appropriate correction is applied to the digital oscillator 181 (i.e. advancing or retarding the digital oscillator 181) until a lock condition is achieved. So, the digital oscillator 181 tracks the incoming drive/reference signal REF and automatically makes adjustments due to clock drift. Once locked, the same control loop maintains a locked condition. Outputs 191, 192 of the digital oscillator 181 are used as the DO (I) and DO (Q) inputs to the processing stage 161. An output of the low-pass filter 184 provides an in-phase component of drive/reference signal REF, called Cr (I). An output of the low-pass filter 185 provides a quadrature component of drive/reference signal REF, called Cr (Q).

Figure 7:
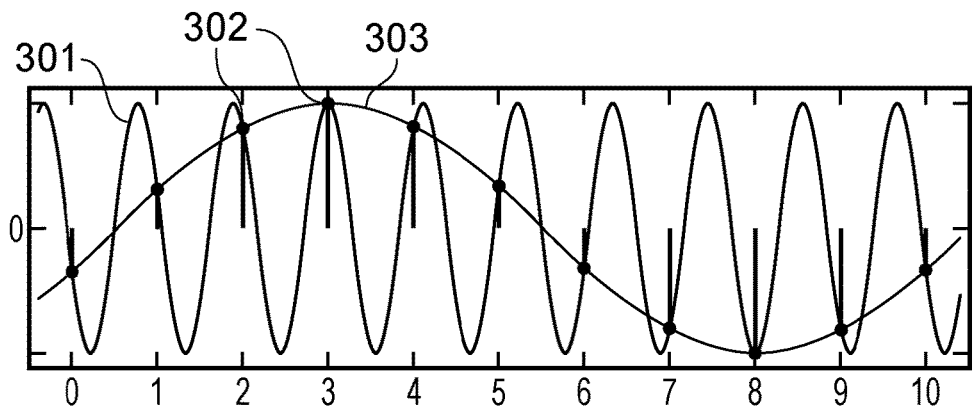
FIG. 7 shows analogue-to-digital sampling.

FIG. 7 shows operation of the ADC 150. In an example of the present invention, the ADC operates at a sampling frequency which is lower than a frequency of the drive/reference signal REF, and therefore lower than a frequency of the signal SENSE received from the sensor cell. FIG. 7 shows signal SENSE 301 and sampling points 302. The resulting signal, after sampling, has a frequency which is a difference between the input signal and the sampling frequency. For example, if the signal 301 has a frequency of 1.05 MHz and the sampling frequency is 1.0 MHz, the sampled signal has a frequency of 50 kHz. Conventional sampling theory recommends a sampling frequency which is at least twice the highest frequency in the sampled signal to avoid aliasing. In the illustrated example, aliasing occurs, as the signal in the sampled/converted data will appear as a much lower sine wave. However, the phase and amplitude of the original signal is preserved in the sampled signal and corresponds to the phase and amplitude of the drive signal. By using an output signal which has a lower frequency than the original signal (e.g. 50 kHz compared to 1.05 MHz) it is possible to process the signal in the digital domain using less computational resources.

Three alternative ways of digital-domain processing will now be described. In a first method, a mathematical model of the apparatus is used to directly calculate values of capacitance (dielectric constant) and resistance (conductivity) from the measured in-phase and quadrature values of the difference signal. In a second method, the measured in-phase and quadrature values of the difference signal are applied to a look-up table to obtain output values of capacitance (dielectric constant) and resistance (conductivity). In a third method, measured in-phase and quadrature values are mapped to a stored set of curves representing capacitance (dielectric constant) and resistance (conductivity). A best fit between the measured I, Q values and one of the curves represents the capacitance (dielectric constant) and resistance (conductivity).

Each of the methods can use the same initial stages of signal processing. The signal processing stages 161, 162 output values representing two complex numbers:
  $c_s$ representing the phase and magnitude of the sense signal, SENSE. $c_s$ comprises an in-phase (real) component $c_s$ (I) and a quadrature (imaginary) component $c_s$ (Q).
  $c_r$ representing the phase and magnitude of the reference signal (i.e. the drive signal, DRIVE/REF). $c_r$ comprises an in-phase (real) component $c_r$ (I) and a quadrature (imaginary) component $c_r$ (Q).

Dividing the two complex measurements [$c_s/c_r$] gives a quantity which is independent of supply voltage or ADC reference voltage variation. Performing this operation also has an effect that if the digital oscillator 181 lags or leads the drive signal by even a small amount, resulting phase shifts are eliminated. This is because the error would apply equally to both drive and sense signals, i.e. a common mode error.

Processing stage 164 determines the difference signal. Performing the division [$c_s/c_r$] gives:
  (i) the phase difference between the sense signal and the drive/reference signal;
  (ii) a magnitude equal to a ratio of the magnitudes of the sense signal and the drive/reference signal.

It should also be noted that the apparatus shown in FIG. 4 with a single ADC 150 and a multiplexer 140 means that the sense and reference signals are not sampled simultaneously. Therefore, it is necessary to multiply the ratio $c_s/c_r$ by another complex quantity to correct for this phase misalignment:

$$c_p = e^{i\omega T}$$

where:
the angular frequency of the drive signal $\omega = 2\pi * 5,050,000$ Hz;
the sampling frequency=2 MHz and the time between sampling channels T=0.5 μs.

The 'output' of the sensor is now a complex quantity A calculated thus:

$$A = \frac{c_p \cdot c_s}{c_r}$$

A is the value that is used in all further analysis.

The following section provides detail of the mathematical model of the apparatus.

Model-Based Method

Input Impedance and Parasitic Properties of the ADC

The input impedance of the ADC 150 will modify the input signal both in amplitude and phase and so its effects need to be calibrated out. The input impedance of the ADC channels is treated as unknown, but it is possible to assume that they are approximately equal since the same ADC is used for measuring both channels, and the inputs are multiplexed.

Figure 8:
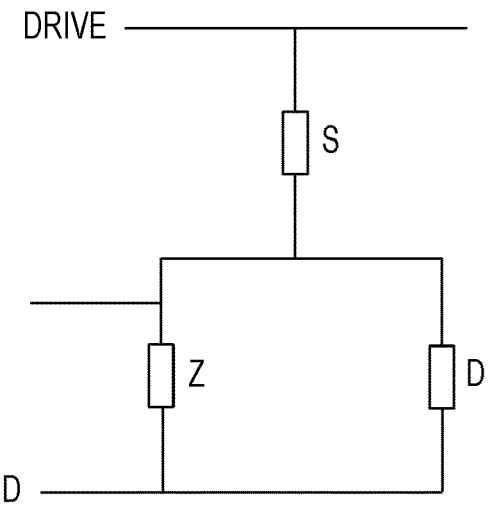
FIG. 8 and FIG. 9 show impedances in the system.

The input impedance of the ADC 150 can be deduced from a process called 'bare-board' calibration. The PCB alone (i.e. the sensor cell is not connected) is powered up and the open-circuit signal measured can be analysed. FIG. 8 shows how the impedances combine generally for both channels, where:

Z is the input impedance of the ADC;
S is a 200 ohm resistor ($R_s = R_{c1}$);
D is a load (to be measured) connected in parallel to the ADC.

Without the cell connected, D→∞ for the sense channel $c_s$, and $D=R_{c2}$ for the reference channel $c_r$. As an example, D=22Ω resistor for a cell filled with cutting fluid. This makes the drive/ref signal and sensor cell have roughly the same impedance when presented to the ADC. It will be understood that D can be set to a value appropriate to the application.

It can be assumed that Z is the same for both channels, and raw sensor output value A can deduce the value of Z.

Network analysis of the above gives:

$$c = \frac{[Z^{-1} + D^{-1}]^{-1}}{[Z^{-1} + D^{-1}]^{-1} + S}$$

which simplifies to:

$$c = \frac{1}{1 + SZ^{-1} + SD^{-1}}$$

Now turn this general form into an expression for $c_s$ and $c_r$:

$$c_s = \frac{1}{1 + SZ^{-1}}$$

since D→∞ and $$c_r = \frac{1}{1 + SZ^{-1} + SD^{-1}}$$

After rearranging and simplification, $c_s/c_r$ can be written as:

$$A = \frac{c_s}{c_r} = \frac{Z + S + ZSD^{-1}}{Z + S}$$

and solved for Z.

$$Z = \frac{S(1 - A)}{A - 1 - SD^{-1}}$$

The value of Z is calculated from the bare-board measurement for each sensor and stored in non-volatile memory for use with all further calculations. This complex quantity represents both the resistive and capacitive loads at the operating frequency.

Deducing the Cell Impedance

Now that the ADC impedance is fully characterised, it is then possible to deduce the impedance of the connected sensor load from further network analysis. The cell impedance is denoted by L. During operation, with the sensor cell connected, the sensor channel output can be written (analogously to our expression for $c_r$) as:

$$c_s = \frac{1}{1 + SZ^{-1} + SL^{-1}}$$

Using the previously derived expression for $c_r$ we can state that:

$$A = \frac{c_s}{c_r} = \frac{1 + SZ^{-1} + SD^{-1}}{1 + SZ^{-1} + SL^{-1}}$$

This can be solved for L to give:

$$L^{-1} = \frac{1}{AS} + \frac{Z^{-1}}{A} + \frac{D^{-1}}{A} - \frac{1}{S} - Z^{-1}$$

This expression combines all of the known resistor values and the calibration value for ADC impedance to give the impedance of the cell and parasitic properties associated with connections to it.

Figure 9:
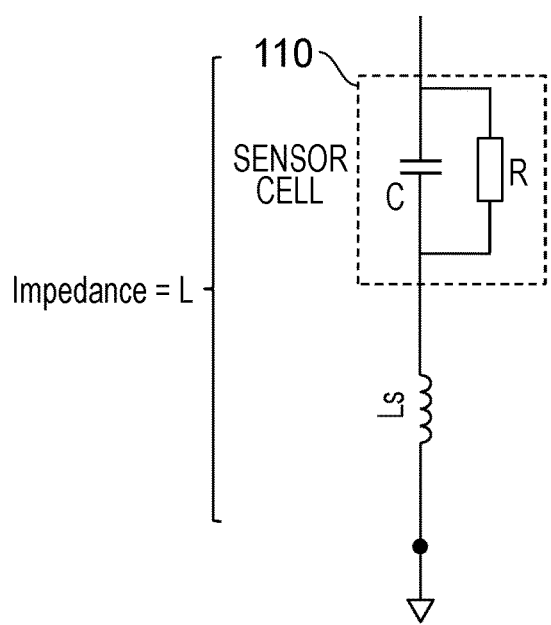

It is assumed now that L represents the impedance of the network shown in FIG. 9 comprising the sensor cell 110 and the lead inductance $L_s$. The contribution of lead inductance $L_s$ is very significant, but it is assumed that its value is constant and it can be determined empirically.

$$L = i\omega L_s + \frac{1}{R^{-1} + i\omega C}$$

Where R is the resistance of the cell and C is its capacitance. R and C can both be deduced from this equation when the value of $L_s$ is known. This is most easily achieved by calculating the cell admittance:

$$Y = \frac{1}{L - i\omega L_s} = R^{-1} + i\omega C$$

$$C = \frac{\text{Im}(Y)}{\omega}$$

from the imaginary part of the admittance, and:

$$R = \frac{1}{\text{Re}(Y)}$$

from the real part.

Calculating Conductivity and Relative Permittivity

The resistance of the cell is determined theoretically by the cell geometry and the resistivity of the fluid as follows:

$$R = \rho \cdot \frac{\ln(b/a)}{2\pi L}$$

where:
ρ is the resistivity of the fluid;
b is the internal diameter of the outer pipe of the cell (e.g. $26.9 \times 10^{-3}$ m);
a is the external diameter of the co-axial rod (e.g. $7 \times 10^{-3}$ m);
L is the length of the rod exposed to the fluid (e.g. $75 \times 10^{-3}$ m).

The cell factor is the ratio of resistance to resistivity. This is calculated to be around 2.85, and measured to be around 2.76 from lab testing with saline fluids of known concentrations.

Conductivity=1/ρ.

Therefore:

Conductivity=2.76/R  (Equation 1)

The capacitance of the cell is calculated to be:

$$C = \frac{2\pi L}{\ln(b/a)} \epsilon_0 \epsilon_r$$

where $\epsilon_0$ is the dielectric permittivity of free space and $\epsilon_r$ is the relative permittivity (dielectric constant) of the fluid.

All of the other dimensions are the same. Hence the experimentally determined cell factor of 2.76 can also be used to develop the relationship between $\epsilon_r$ and capacitance in a similar way such that:

$\epsilon_r = 2.76 C/\epsilon_0$  (Equation 2)

From the above description, it will be understood that the measured values $c_s$, $c_r$ (converted to the complex difference signal quantity A) are input to a mathematical model of the apparatus which includes at least one parasitic component, to provide an output value of conductivity (Equation 1) and dielectric constant (Equation 2). Another possible property is complex permittivity.

Determination of Lead Inductance and Other Parasitic Elements

The lead inductance can be determined empirically. If the expression for L is rewritten using discrete real and imaginary parts, it can be seen that the contribution of $L_s$ to the final measurement is small when cell resistance is high, and plays a significant part when the cell resistance is low. By passing de-ionised water through the cell, it is possible to measure a value for the cell capacitance by assuming lead-inductance to be zero in the above analysis.

Passing saline solutions of varying concentrations through the sensor at a constant temperature should give a constant value for capacitance and varying values of conductivity. A value of lead inductance was chosen to give the flattest possible response for capacitance over this range.

However, the response is not perfect, as it is likely that there are additional parasitic components yet to be identified and the network analysis needs further refinement.

Figure 10:
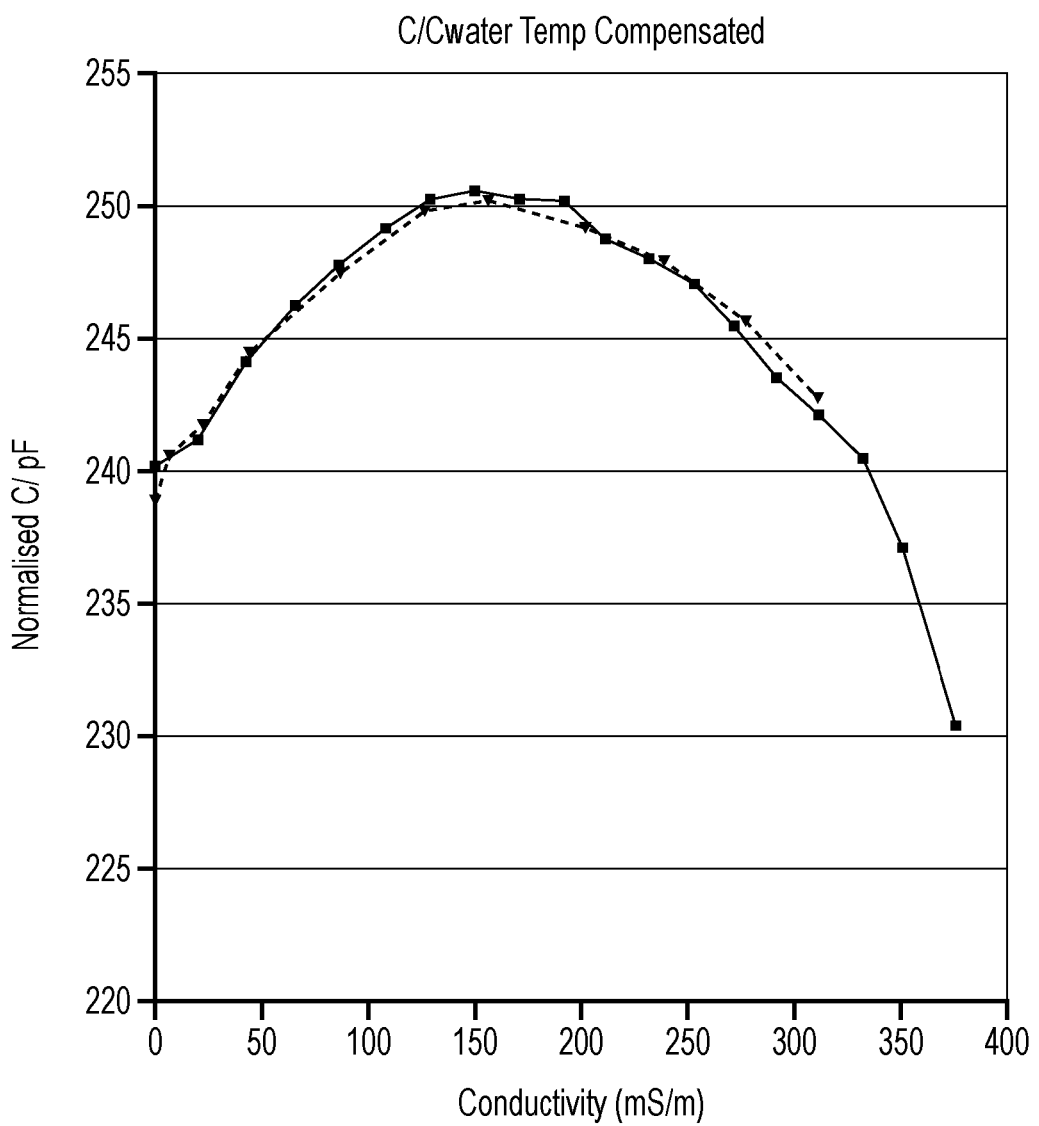
FIG. 10 shows a graph of capacitance versus conductivity for a test fluid.

FIG. 10 shows two sets of measurements performed on varying concentrations of saline. It can be seen that there are deviations from the ideal flat horizontal line even when lead inductance is considered. Therefore, for practical applications, it is possible to store a map of this saline data and interpolate these values to provide calibration information for different conductivities.

Look-Up Table Method

The look-up table method uses the difference signal determined by stage 164. As described above, the quantity A can be used:

$$A = \frac{c_p \cdot c_s}{c_r}$$

where:
$c_s$ represents the phase and magnitude of the sense signal, SENSE. $c_s$ comprises an in-phase (real) component $c_s$ (I) and a quadrature (imaginary) component $c_s$ (Q).
$c_r$ represents the phase and magnitude of the reference signal (i.e. the drive signal, DRIVE/REF). $c_r$ comprises an in-phase (real) component $c_r$ (I) and a quadrature (imaginary) component $c_r$ (Q).
$c_p$ is a correction factor to compensate for the different times at which $c_s$ and $c_r$ are sampled.

Processing stage 165 then uses the in-phase and quadrature components of the complex difference signal quantity A to look up corresponding values of C (dielectric constant) and R (conductivity) in a stored set of data, i.e. a look-up table.

Data Mapping Method

The data mapping method uses the difference signal determined by stage 164. As described above, the quantity A can be used:

$$A = \frac{c_p \cdot c_s}{c_r}$$

where:
$c_s$ represents the phase and magnitude of the sense signal, SENSE. $c_s$ comprises an in-phase (real) component $c_s$ (I) and a quadrature (imaginary) component $c_s$ (Q).
$c_r$ represents the phase and magnitude of the reference signal (i.e. the drive signal, DRIVE/REF). $c_r$ comprises an in-phase (real) component $c_r$ (I) and a quadrature (imaginary) component $c_r$ (Q).
$c_p$ is a correction factor to compensate for the different times at which $c_s$ and $c_r$ are sampled.

Figure 11:
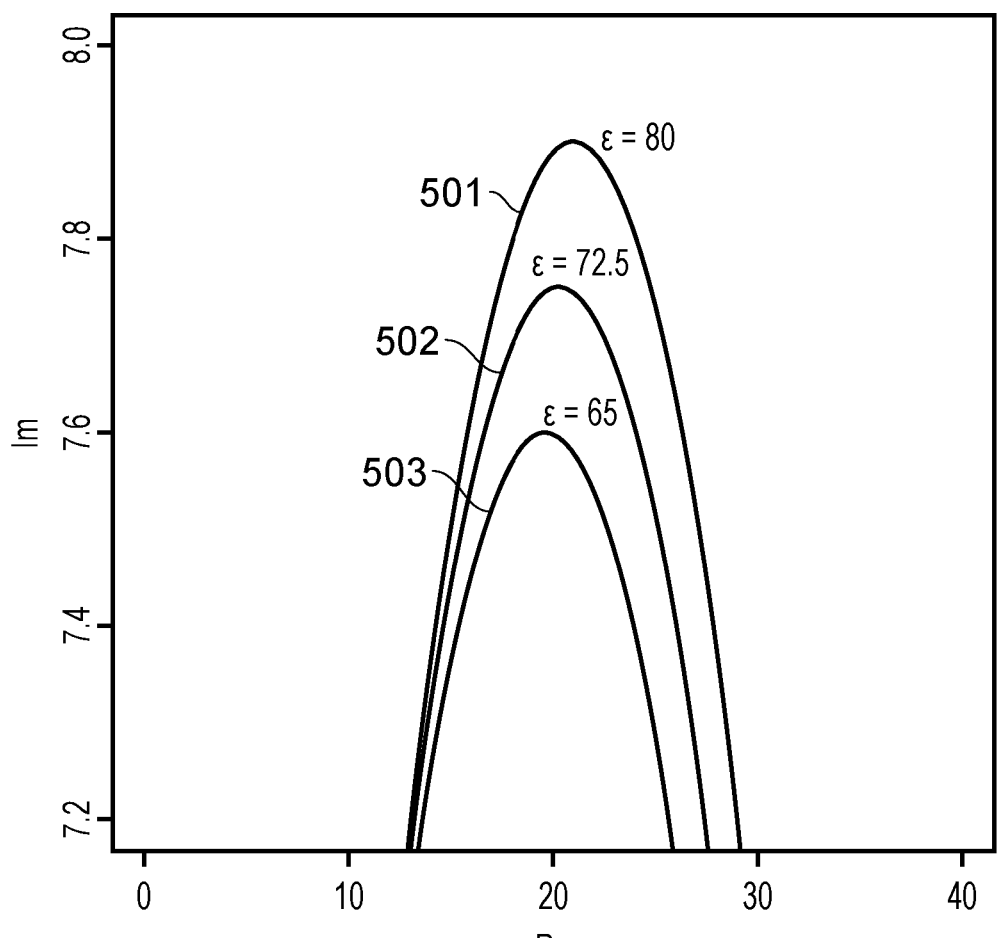
FIG. 11 shows a set of curves which can be used to map in-phase and quadrature components to dielectric constant and conductivity.

Processing stage 165 then maps the in-phase and quadrature components of the complex difference signal quantity A to (or compares it to) a stored set of data. The stored data may be in the form of a set of curves. FIG. 11 shows a set of curves 501, 502, 503 representing fluids of three different dielectric constants and varying conductivity. All values are approximate and are to represent the concept only. A 'measurement' in the form of a pair of values I, Q will be represented by a point on this map of data. To deduce the emulsion concentration therefore it is possible to empirically deduce concentration and dielectric constant from the position of a point on this map. For a given measurement (I, Q) it is possible by extrapolation to work out the dielectric constant to within enough precision for monitoring emulsion cutting fluid concentration with varying amounts of ionic contamination.

Figure 12:
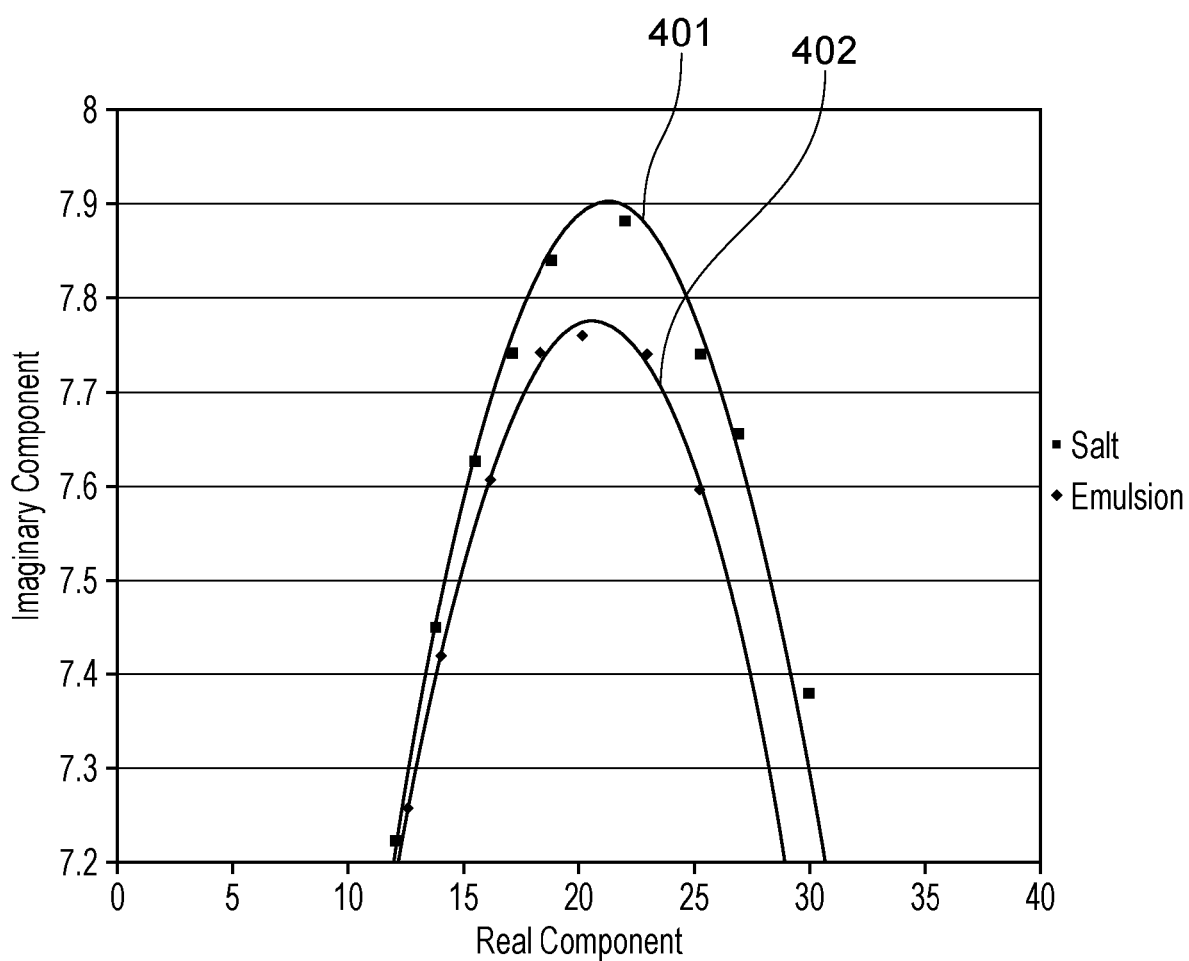
FIG. 12 shows data to illustrate in-phase and quadrature components vary with fluid properties.

FIG. 12 shows experimental data from measurements at 5.05 MHz at 20 degrees Celsius of various solutions of brine (dielectric constant assumed to be unchanged) 401 and emulsion (with varying conductivity and dielectric constant) 402. The data illustrates the transformation effect of the parasitic circuit elements. Curve 401 represents a fluid which has unchanging dielectric constant, but varying conductivity. This curve can be considered as a type of control which shows how the parasitic effects 'warp' the mapping of the real and imaginary components away from a perfect theoretical straight horizontal line. Curve 402 represents fluids with both variations in dielectric constant and conductivity. A test fluid was formed by adding varying amounts of cutting fluid emulsion mixture to deionised water. In this case, the emulsion concentration is varied between 2.5 and 20%. The conductivity is seen to increase with increasing concentration (right to left), but also the dielectric constant is reduced from an expected value of ~77.5 at 2.5% to ~60 at 20%.

The convergence of the data on the left hand side is due to the mathematical effect of increasing conductivity causing a reduction of the sensitivity of the system to the effects being measured.

Accurate Conductivity Measurements

Using a drive signal of 1.05 MHz or lower, the reactive (capacitive and parasitic components) of the signal are significantly reduced. Under these conditions the real part of the signal can be used to deduce conductivity without making assumptions about the parasitic effects of the circuit. For a system where it is not expected that temperature or fluid composition changes quickly, this measurement can be made near simultaneously to the high frequency measurement.

Reference Signal (REF)

A refinement of the design is the use of a reference signal REF. This design uses Rc1 and Rc2 to represent a 'virtual' purely resistive cell. It will have an amplitude in phase with the drive signal. REF can provide a better reference signal than DRIVE, as it is designed to have a similar output impedance to SENSE. The thinking behind this is that if the phase shift caused by the ADC input capacitance was identical for each channel, its effect would cancel out. This ideal situation is unlikely to be achieved, but this approach will help to reduce the effect of the input capacitance.

Example Fluids

An example application of the apparatus is to control the mixture and composition of emulsion cutting fluids. The proportion of oil to water is to be controlled. The ratio of oil to water can be determined by measuring the dielectric constant of the fluid. Water has a dielectric constant of around 80 at 20 degrees Celsius, and the oil component has a dielectric constant <10. Evaporation of water from the fluid causes the oil to water ratio to increase, and so it is necessary to add water to keep the emulsion concentration within the required limits.

Dielectric constant of the fluid is approximately equal to the average by volume of the two components, so for a 10% mix we would expect to see a dielectric constant of around 72. The surfactant used to keep the oil droplets in suspension is conductive as it has ionic components. Conductivity alone cannot be used to determine the emulsion concentration, as conductivity is affected by other factors such as water hardness and other ionic contamination.

The dielectric constant of water varies with temperature. Therefore, it is also desirable to measure temperature and make an appropriate compensation. FIG. 1 shows a temperature sensor 105 located with the fluid sensor cell 110. An output indicative of temperature is provided to the signal processing 130.

Other possible applications are monitoring the proportion of water in any chemical mixture (flowing or static), such as: beer/whiskey manufacturing (e.g. to determine alcohol content); bio-fuel manufacture (e.g. to monitor for water contamination); gearbox oil and lubricant monitoring.

Another possible application is measuring humidity of a gas.

Other Alternatives

The apparatus may use a single ADC and a multiplexer to time multiplex input signals to the single ADC, as shown in FIG. 4. Alternatively, the apparatus may comprise two separate ADCs, with one ADC per input signal.

The frequency of the drive signal may be selected based on the type of fluid under test. In other examples, the drive signal generator may generate a plurality of drive signals at different frequencies, or there may be a plurality of drive signal generators.

Figure 13:
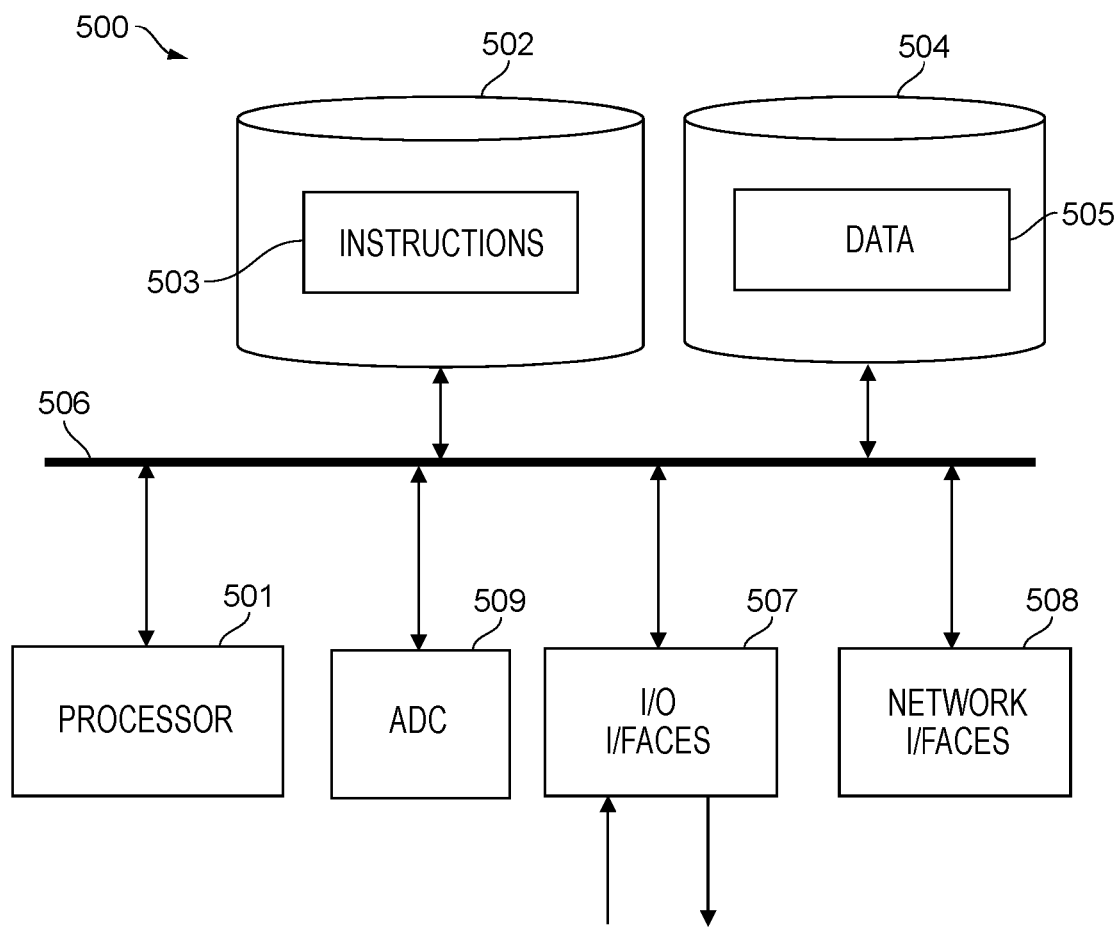
FIG. 13 show a processing apparatus.

FIG. 13 shows an example of processing apparatus 500 which may be implemented as any form of a computing and/or electronic device, and in which embodiments of the system and methods described above may be implemented. Processing apparatus may implement all, or part of, any of the methods described above. Processing apparatus 500 comprises one or more processors 501 which may be microcontrollers, microprocessors, controllers or any other suitable type of processors for executing instructions to control the operation of the device. The processor 501 is connected to other components of the device via one or more buses 506. Processor-executable instructions 503 may be provided using any computer-readable media, such as memory 502. The processor-executable instructions 503 can comprise instructions for implementing the functionality of the described methods. The memory 502 is of any suitable type such as read-only memory (ROM), random access memory (RAM), a storage device of any type such as a magnetic or optical storage device. Additional memory 504 can be provided to store data 505 used by the processor 501. The processing apparatus 500 comprises input/output (I/O) interfaces 507. The I/O interfaces 507 can receive the input signals from the sensor cell. The I/O interfaces 507 can output signals indicating the measured properties of the fluid. The processing apparatus 500 comprises one or more ADCs to sample analogue input signals, as described above. The processing apparatus 500 comprises one or more network interfaces 508 for interfacing with other network entities. The processing apparatus 500 may be implemented as a microcontroller with a processor 501, memory 502, I/O interfaces 507 and ADC 509 integrated onto a single integrated circuit.

Figure 14B:
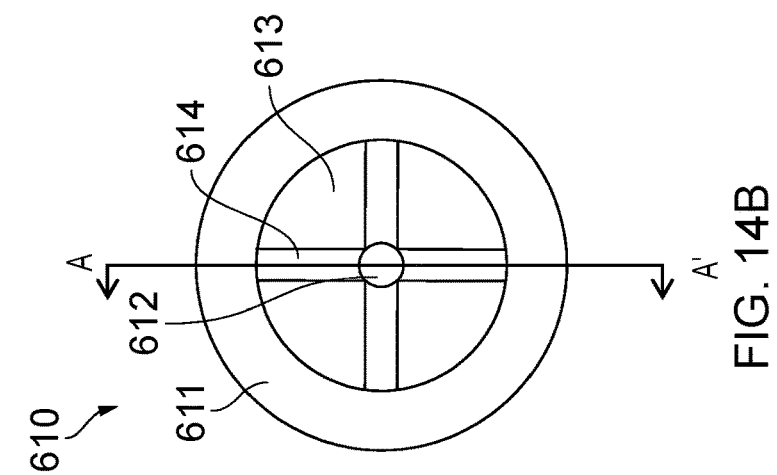
FIG. 14 shows an example fluid sensor.
Figure 14A:
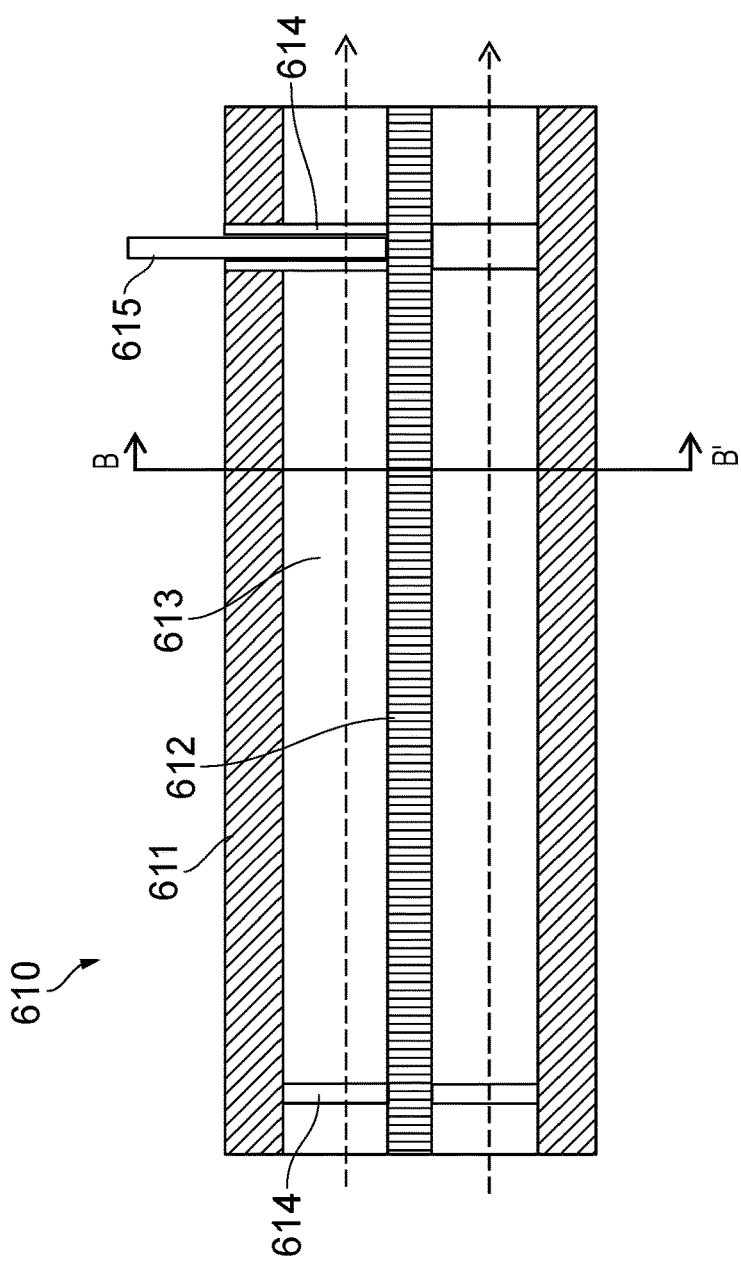

FIGS. 14A and 14B show an example of a fluid sensor 610 which can be used as the fluid sensor cell 110 in any of the examples or embodiments described above. FIG. 14A shows the fluid sensor 610 in cross-section along a longitudinal axis (A-A' in FIG. 14B). FIG. 14B shows the fluid sensor 610 in cross-section along line B-B' of FIG. 14A. The fluid sensor 610 is configured for monitoring a flowing fluid. The fluid sensor 610 is a form of capacitive sensor. The sensor has a first, outer, electrode 611 and a second, inner, electrode 612. The outer electrode 611 is tubular. The inner electrode 612 is a cylindrical rod. The electrodes 611, 612 are coaxial. A fluid flow channel 613 is defined in the region between the electrodes 611, 612. Fluid can flow along the fluid flow channel 613. This allows measurements to be made without a need to interrupt a process which uses the fluid. For example, in the application of measuring a cutting fluid, the cutting fluid (or a portion of the cutting fluid) can be routed via the flow channel 613. A feed through conductor 615 connects the inner electrode 612 to a drive signal generator located outside the fluid sensor. The conductor 615 is insulated. A plurality of supports 614, shown here in the form of a cross-shaped array, support the inner electrode 612 within the outer electrode. The supports 614 are formed of an insulating material. The flow channel 613 extends through apertures between the supports 614. A set of supports 614 may be located near to each longitudinal end of the fluid sensor, as shown in FIG. 14A. As shown in FIG. 14A, one of the sets of supports 614 may incorporate the feed through conductor 615. The support 614 around the feed through conductor 615 provides a fluid-tight seal to prevent fluid loss from the sensor 610. This configuration avoids the need for a set of supports 614 and a separate tubular element for the feed through conductor 615. The fluid sensor 610 can have any suitable length and diameter.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. An apparatus for measuring at least one property of a fluid, the apparatus comprising:
    a capacitive fluid sensor comprising a first electrode and a second electrode with a sensing region between the electrodes;
    an alternating signal source configured to apply an alternating drive signal to the capacitive fluid sensor; and
    a processing apparatus configured to:
        receive a sense signal from the capacitive fluid sensor;
        receive the alternating drive signal;
        determine a complex difference signal comprising a ratio of the sense signal and the drive signal, the complex difference signal comprising an in-phase difference component and a quadrature difference component;
        determine the at least one property of the fluid based on both the in-phase phase difference component and the quadrature difference component of the difference signal by compensating for an effect on the complex difference signal due to at least one parasitic element of the apparatus.

2. The apparatus according to claim 1 wherein the processing apparatus is configured to determine an in-phase component of the sense signal and a quadrature component of the sense signal.

3. The apparatus according to claim 2 wherein the processing apparatus is configured to determine the in-phase component of the sense signal and the quadrature component of the sense signal by an averaging filtering operation performed over a plurality of cycles of the alternating drive signal.

4. The apparatus according to claim 1 wherein the processing apparatus is configured to determine an in-phase component of the drive signal and a quadrature component of the drive signal.

5. The apparatus according to claim 1 wherein the processing apparatus is configured to determine an in-phase component of the drive signal and a quadrature component of the drive signal by an averaging filtering operation performed over a plurality of cycles of the alternating drive signal.

6. The apparatus according to claim 1 wherein the processing apparatus is configured to:
    determine the in-phase component of the sense signal and the quadrature component of the sense signal by an averaging filtering operation performed over a plurality of cycles of the alternating drive signal;
    determine an in-phase component of the drive signal and a quadrature component of the drive signal by an averaging filtering operation performed over a plurality of cycles of the alternating drive signal;
    determine the in-phase difference component based on the filtered in-phase component of the sense signal and the filtered in-phase component of the drive signal; and
    determine the quadrature difference component based on the filtered quadrature component of the sense signal and the filtered quadrature component of the drive signal.

7. The apparatus according to claim 1 wherein the processing apparatus is configured to use the in-phase difference component and the quadrature difference component in an algorithmic model of the apparatus to determine the dielectric constant of the fluid, wherein the algorithmic model includes the at least one parasitic element of the apparatus.

8. The apparatus according to claim 1 wherein the processing apparatus is configured to use the in-phase difference component and the quadrature difference component in an algorithmic model of the apparatus to determine conductivity of the fluid, wherein the algorithmic model includes the at least one parasitic element of the apparatus.

9. The apparatus according to claim 1 wherein the processing apparatus is configured to measure at least one property of a fluid with a conductivity of up to 200 mS/m.

10. The apparatus according to claim 1 wherein the processing apparatus is configured to sample the sense signal at a sampling frequency, and a frequency of the alternating current drive signal is higher than the sampling frequency.

11. The apparatus according to claim 1 wherein the processing apparatus is configured to:
provide a digital oscillator with an in-phase oscillator output and a quadrature oscillator output;
provide a phase-locked loop which is configured to use the in-phase oscillator output and the quadrature oscillator output to achieve synchronisation between the drive signal and the digital oscillator.

12. The apparatus according to claim 11 wherein the phase-locked loop is a Costas loop.

13. The apparatus according to claim 11 wherein, the processing apparatus is configured to use the in-phase oscillator output and the quadrature oscillator output to process the sense signal when a locked synchronisation state has been achieved.

14. The apparatus according to claim 1 comprising an analogue-to-digital converter and wherein the processing apparatus is configured to:
sample the sense signal at a first time and sample the drive signal at a second time which is offset from the first time; and
apply a correction factor to the sampled signals to correct for the offset times at which the signals were sampled.

15. The apparatus according to claim 1 wherein the parasitic element is lead inductance.

16. The apparatus according to claim 1 wherein the processing stage is a digital signal processing stage.

17. The apparatus according to claim 1 comprising a temperature sensor, and wherein the processing apparatus is configured to:
determine temperature of the fluid;
determine conductivity using the determined temperature.

18. The apparatus according to claim 1 wherein the capacitive fluid sensor is configured to monitor a flowing fluid, wherein the first electrode and the second electrode define a fluid flow channel between the electrodes.

19. A processing apparatus for measuring at least one property of a fluid, the processing apparatus configured to:
receive a sense signal from a capacitive fluid sensor;
receive an alternating drive signal which has been applied to the capacitive fluid sensor;
determine a complex difference signal comprising a ratio of the sense signal and the drive signal, the complex difference signal comprising an in-phase difference component and a quadrature difference component;
determine the at least one property of the fluid based on both the in-phase phase difference component and the quadrature difference component of the difference signal by compensating for an effect on the complex difference signal due to at least one parasitic element of the apparatus.

20. A method of measuring at least one property of a fluid, the method comprising:
receiving a sense signal from a capacitive fluid sensor;
receiving an alternating drive signal which has been applied to the capacitive fluid sensor;
determining a complex difference signal comprising a ratio of the sense signal and the drive signal, the complex difference signal comprising an in-phase difference component and a quadrature difference component;
determining the at least one property of the fluid based on both the in-phase phase difference component and the quadrature difference component of the difference signal by compensating for an effect on the complex difference signal due to at least one parasitic element of the apparatus.

* * * * *